US009266796B2

(12) United States Patent
Corradi et al.

(10) Patent No.: US 9,266,796 B2
(45) Date of Patent: Feb. 23, 2016

(54) SYSTEMS AND METHODS FOR PRODUCING DESIRED XYLENE ISOMERS

(71) Applicant: UOP LLC, Des Plaines, IL (US)

(72) Inventors: Jason T. Corradi, Arlington Heights, IL (US); Gregory Werba, Arlington Heights, IL (US); Rajeswar Gattupalli, Arlington Heights, IL (US)

(73) Assignee: UOP LLC, Des Plaines, IL (US)

( * ) Notice: Subject to any disclaimer, the term of this patent is extended or adjusted under 35 U.S.C. 154(b) by 302 days.

(21) Appl. No.: 14/040,391

(22) Filed: Sep. 27, 2013

(65) Prior Publication Data

US 2015/0094509 A1    Apr. 2, 2015

(51) Int. Cl.
*C07C 7/09* (2006.01)
*C07C 7/00* (2006.01)
*C07C 5/27* (2006.01)

(52) U.S. Cl.
CPC ............... *C07C 7/005* (2013.01); *C07C 5/2729* (2013.01); *C07C 5/2732* (2013.01); *C07C 7/09* (2013.01)

(58) Field of Classification Search
None
See application file for complete search history.

(56) References Cited

U.S. PATENT DOCUMENTS

| 2,621,149 | A | 12/1952 | Scott et al. |
|---|---|---|---|
| 4,381,419 | A | 4/1983 | Wylie |
| 4,442,222 | A | 4/1984 | Smolin et al. |
| 6,600,083 | B2 | 7/2003 | Doyle et al. |
| 7,271,305 | B2 | 9/2007 | Williams et al. |
| 7,687,674 | B2 | 3/2010 | Wegerer |
| 7,727,490 | B2 | 6/2010 | Zhou |
| 8,084,657 | B2 | 12/2011 | Kong et al. |
| 8,198,502 | B2 | 6/2012 | Bresler et al. |
| 8,323,581 | B2 | 12/2012 | Bresler et al. |
| 2002/0082462 | A1 | 6/2002 | Ferraro et al. |
| 2011/0319688 | A1 | 12/2011 | Ou |
| 2012/0047889 | A1 | 3/2012 | Ulas Acikgoz et al. |
| 2012/0048720 | A1 | 3/2012 | Werba et al. |

*Primary Examiner* — Tam M Nguyen

(57) ABSTRACT

Methods and systems are provided for producing a desired xylene isomer. The method includes adsorbing the desired xylene isomer from a mixed xylene stream in an adsorbent chamber. The desired xylene isomer is desorbed with a desorbent to produce an extract stream with the desired xylene isomer and the desorbent, where the desorbent has a lower boiling point than the desired xylene isomer. The extract stream is fractionated in an extract fractionator to produce a low pressure extract overhead stream with gaseous desorbent. The low pressure extract overhead stream is pressurized to produce a high pressure extract overhead stream with a temperature greater than an extract reboiler temperature. The high pressure extract overhead stream is condensed in an extract process reboiler, and produces a liquid extract overhead stream.

19 Claims, 2 Drawing Sheets

SYSTEMS AND METHODS FOR PRODUCING DESIRED XYLENE ISOMERS

TECHNICAL FIELD

The present disclosure generally relates to systems and methods for producing desired isomers of xylene, and more particularly relates to systems and methods for recovering heat during xylene isomer fractionations in a xylene isomer recovery process.

BACKGROUND

Xylene isomers are important intermediates in chemical syntheses, and specific xylene isomers are desired for different processes. Paraxylene is a feedstock for terephthalic acid, and terephthalic acid is used in the manufacture of synthetic fibers and resins. Metaxylene is used in the manufacture of certain plasticizers, azo dyes, and wood preservatives. Orthoxylene is a feedstock for phthalic anhydride production, and phthalic anhydride is used in the manufacture of certain plasticizers, dyes, and pharmaceutical products.

Desired xylene isomers typically are separated from mixed xylene streams by using an adsorbent selective to the desired isomer. The desired isomer is adsorbed, and the remaining isomers are discharged in a mixed raffinate stream. A desorbent is then used to desorb the desired xylene isomer, and the desorbent and desired xylene isomer are collected and separated by distillation (also referred to as fractionation). The desorbents are typically referred to as either heavy or light, where a heavy desorbent has a higher molecular weight and a higher boiling point than xylene and a light desorbent has a lower molecular weight and a lower boiling point than xylene. Xylene isomer recovery systems with heavy desorbents tend to use less energy than systems with light desorbents, because the desorbent does not need to be repeatedly evaporated and lifted in the fractionation step. However, heavy desorbent systems require stringent feed purity to control accumulation of undesired compounds in the recycled desorbent. The undesired compounds are impurities that reduce the desorbent effectiveness and product purity. Additional equipment is needed to maintain the heavy desorbent purity during the desorbent recycling process. The distillation columns in heavy desorbent systems have higher reboiler temperatures, which leads to higher operating pressures. The higher operating pressures require higher pressure ratings for the equipment involved, which increase the equipment capital cost.

A light desorbent system allows a relaxed feed specification relative to a heavy desorbent system. This helps to offset the increased energy costs associated with recovering light desorbent as a distillation column overhead stream. The light desorbent systems also provide substantial savings in the total equipment count for xylene recovery systems, because the additional equipment for purifying and storing the desorbent is not needed. The light desorbent xylene recovery systems also have lower distillation column operating pressures, so thinner shell thicknesses and lower pressure ratings can be used to further reduce capital costs for installing new systems. Toluene is one example of a light desorbent that can be used, and toluene is less expensive than many of the heavy desorbents available.

Energy is required to evaporate the light desorbent during distillation. Fuel is typically burned to provide the heat energy for operating the distillation columns, but in some embodiments, electrical power is less expensive than heat produced by combusting fuel. Electrical energy can be used for evaporating the light desorbent in the distillation reboiler by using a heat pump to recover heat from the overhead stream. The heat pump transfers some of the energy for distillation from the burning of fuel to the use of electrical power.

Accordingly, it is desirable to develop methods and systems for producing desired xylene isomers from mixed xylene streams using a heat pump to recover energy from the distillation column overheads. In addition, it is desirable to develop methods and systems for producing desired xylene isomers while minimizing the burning of fuel for energy. Furthermore, other desirable features and characteristics of the present embodiment will become apparent from the subsequent detailed description and the appended claims, taken in conjunction with the accompanying drawings and this background.

BRIEF SUMMARY

A method is provided for producing a desired xylene isomer. The method includes adsorbing the desired xylene isomer from a mixed xylene stream in an adsorbent chamber. The desired xylene isomer is desorbed with a desorbent to produce an extract stream with the desired xylene isomer and the desorbent, where the desorbent has a lower boiling point than the desired xylene isomer. The extract stream is fractionated in an extract fractionator to produce a low pressure extract overhead stream with gaseous desorbent. The low pressure extract overhead stream is pressurized to produce a high pressure extract overhead stream with a temperature greater than an extract reboiler temperature. The high pressure extract overhead stream is condensed in an extract process reboiler, and produces a liquid extract overhead stream.

Another method is also provided for producing a desired xylene isomer. The method includes fractionating a mixed raffinate stream in a raffinate fractionator to produce a low pressure raffinate overhead stream including gaseous desorbent and a raffinate xylene isomer stream including raffinate xylene isomers different than the desired isomer. The low pressure raffinate overhead stream is pressurized to produce a high pressure raffinate overhead stream with a temperature above a raffinate reboiler temperature. The high pressure raffinate overhead stream is condensed in a raffinate process reboiler, which produces a liquid raffinate overhead stream. The isomerization stream is isomerized in an isomerization unit to produce the desired xylene isomer.

A system is also provided for producing the desired xylene isomer. The system includes an adsorbent chamber suitable for containing a selective adsorbent, where the selective adsorbent is selective to the desired xylene isomer. An extract fractionator is coupled to the adsorbent chamber, where the extract fractionator includes an extract process reboiler, and an extract overhead receiver. An extract compressor is coupled to the extract overhead receiver and the extract process reboiler, and configured to raise the pressure and temperature of a gas between the extract overhead receiver and the extract process reboiler.

BRIEF DESCRIPTION OF THE DRAWINGS

The present embodiment will hereinafter be described in conjunction with the following drawing figures, wherein like numerals denote like elements, and wherein.

DETAILED DESCRIPTION

The following detailed description is merely exemplary in nature and is not intended to limit the application and uses of the embodiment described. Furthermore, there is no intention to be bound by any theory presented in the preceding background or the following detailed description.

The various embodiments described herein relate to systems and methods for producing a desired xylene isomer from a mixed xylene feedstock. A feed stream is fractionated in a feed fractionator to produce a mixed xylene stream with hydrocarbons containing 8 carbons (referred to herein as C8 compounds). The mixed xylene stream is fed into an adsorbent chamber with a selective adsorbent that preferentially adsorbs a desired xylene isomer. A desorbent is fed into the adsorbent chamber to displace the desired xylene isomer, which exits the adsorbent chamber in an extract stream. The other xylene isomers pass from the adsorbent chamber in a mixed raffinate stream including the raffinate xylene isomers and the desorbent. The desorbent is separated from the desired xylene isomer in an extract fractionator, and a heat pump is used to recover energy from an extract overhead stream to evaporate extract column bottoms in an extract process reboiler. The overhead stream is pressurized, which increases the temperature to above the temperature in the extract process reboiler, and then condensed in the extract process reboiler. A similar heat pump can also be used to recover desorbent from the mixed raffinate stream.

Figure 1:
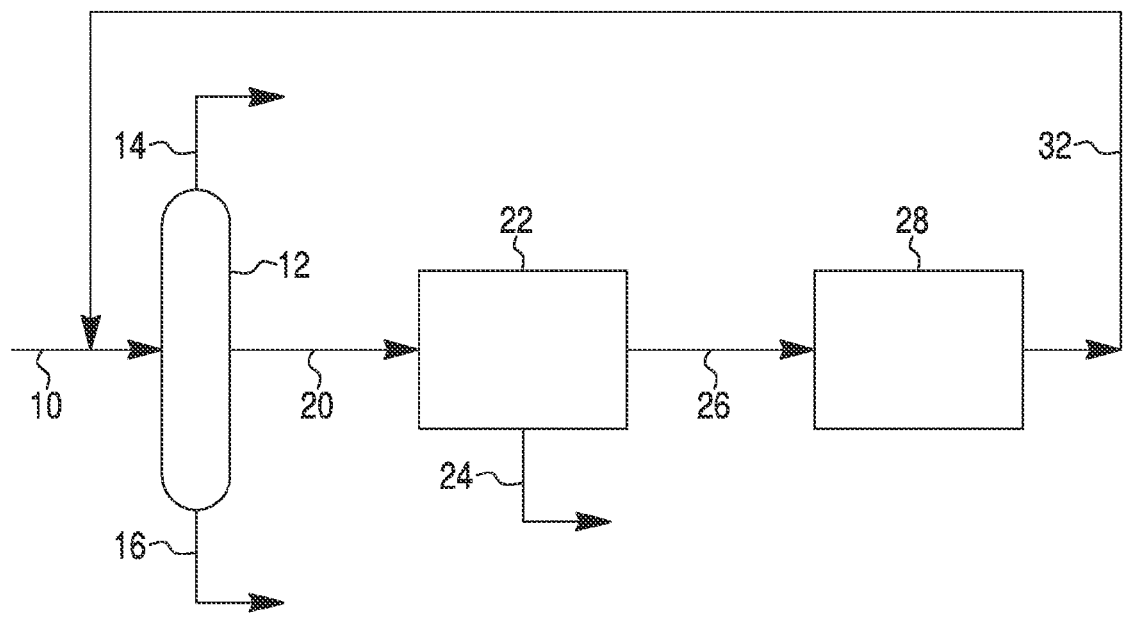
FIG. 1 is a schematic diagram of an exemplary embodiment of a xylene isomer production system and method for producing xylene isomers.

Reference is now made to an exemplary embodiment of a xylene isomer product system in FIG. 1. A feed stream 10 is fed to a feed fractionator 12 to produce a feed fractionator overhead stream 14, a feed fractionator bottoms stream 16, and a mixed xylene stream 20. The feed fractionator overhead stream 14 includes hydrocarbons with 7 carbons or less (C7−), the feed fractionator bottoms stream 16 includes hydrocarbons with 9 carbons or more (C9+), and the mixed xylene stream 20 includes hydrocarbons with 8 carbons (C8). The different fractions (such as C7−, C8, and C9+) are separated based on the relative boiling points of the compounds present. The feed fractionator 12 can be operated from a pressure of about 5 kilo Pascals absolute (kPa) to about 1,800 kPa (about 0.7 pounds per square inch absolute (PSIA) to about 260 PSIA), and a temperature from about 35 degrees centigrade (° C.) to about 360° C. (about 65 degrees Fahrenheit (° F.) to about 680° F.). The feed stream 10 has a relatively high concentration of aromatic compounds, such as about 40 to about 100 mass percent.

Suitable feed streams 10 for producing a desired xylene isomer are available from many sources. For example, a fluid catalytic cracking (FCC) unit and fractionator, when run in high severity mode, can produce a fraction with hydrocarbons having 7 to 10 carbons (C7-10), where about 60 mass percent of the hydrocarbons are aromatic. Certain coal liquefaction processes produce hydrocarbon streams rich in aromatic compounds, and these hydrocarbon streams are suitable for use as the feed stream 10. Other possible sources include various petroleum refining processes, thermal or catalytic cracking of hydrocarbons, or petrochemical conversion processes, including hydrocarbon streams processed in a reformer using a catalyst designed to produce aromatic compounds. Additional processing steps (not illustrated) can be used to remove non-aromatic compounds from the feed stream 10 or the mixed xylene stream 20 in some embodiments, such as liquid extraction, extractive crystallization, clay treating, or additional fractionation.

The mixed xylene stream 20 is introduced into an isomer recovery unit 22 that produces a desired xylene isomer stream 24 and a raffinate xylene isomer stream 26, as described more fully below. The raffinate xylene isomer stream 26 is introduced into an isomerization unit 28 where the raffinate xylene isomers, which are the xylene isomers other than the desired xylene isomer, are isomerized to produce more of the desired xylene isomer. The desired xylene isomer was removed in the isomer recovery unit 22, and the removal of one isomer shifts the composition of the raffinate xylene isomer stream 26 away from equilibrium. The raffinate xylene isomer stream 26 therefore primarily includes 2 of the 3 xylene isomers, so the desired xylene isomer, which is the isomer primarily absent from the raffinate xylene isomer stream 26, is produced in the isomerization unit 28 to bring the mixture closer to an equilibrium ratio. The equilibrium ratio is about 20 to 25 percent orthoxylene, 20 to 30 percent paraxylene, and 50 to 60 percent metaxylene at about 250° C., and this equilibrium ratio varies with temperature and other conditions.

In an exemplary embodiment, the isomerization unit 28 includes an isomerization catalyst 30, and operates at suitable isomerization conditions. Suitable isomerization conditions include a temperature from about 100° C. to about 500° C. (about 200° F. to about 900° F.), or from about 200° C. to about 400° C. (about 400° F. to about 800° F.), and a pressure from about 500 kPa to about 5,000 kPa (about 70 PSIA to about 700 PSIA). The isomerization unit 28 includes a sufficient volume of isomerization catalyst to provide a liquid hourly space velocity, with respect to the raffinate xylene isomer stream 26, from about 0.5 to about 50 $hr^{-1}$, or from about 0.5 to about 20 $hr^{-1}$. Hydrogen may be present at up to about 15 moles of hydrogen per mole of xylene, but in some embodiments hydrogen is essentially absent from the isomerization unit 28. The isomerization unit 28 may include one, two, or more reactors, where suitable means are employed to ensure a suitable isomerization temperature at the entrance to each reactor. The xylenes are contacted with the isomerization catalyst in any suitable manner, including upward flow, downward flow, or radial flow.

The isomerization catalyst includes a zeolitic aluminosilicate with a $Si:Al_2$ ratio greater than about 10/1, or greater than about 20/1 in some embodiments, and a pore diameter of about 5 to about 8 angstroms. Some examples of suitable zeolites include, but are not limited to, MFI, MEL, EUO, FER, MFS, MTT, MTW, TON, MOR, and FAU, and gallium may be present as a component of the crystal structure. In some embodiments, the $Si:Ga_2$ mole ratio is less than 500/1, or less than 100/1 in other embodiments. The proportion of zeolite in the catalyst is generally from about 1 to about 99 weight percent, or from about 25 to about 75 weight percent. In some embodiments, the isomerization catalyst includes about 0.01 to about 2 weight percent of one or more of ruthenium (Ru), rhodium (Rh), palladium (Pd), osmium (Os), Iridium (Ir), and platinum (Pt), but in other embodiments the isomerization catalyst is substantially absent of any metallic compound, where substantial absence is less than about 0.01 weight percent. The balance of the isomerization catalyst is an inorganic oxide binder, such as alumina, and a wide variety of catalyst shapes can be used, including spherical or cylindrical.

An isomerized stream 32 exits the isomerization unit 28 and returns to the isomer recovery unit 22, so some material is recycled and repeatedly passes between the isomer recovery unit 22 and the isomerization unit 28. The isomerized stream 32 may be passed through the feed fractionator 12 in some embodiments (as shown), so C8 compounds that were changed to a compound with a different number of carbons in the isomerization unit 28 can be removed from the loop. The isomerized stream 32 includes more of the desired xylene isomers than in the raffinate xylene isomer stream 26, so more of the desired xylene isomer is available for recovery. In this manner, the total amount of the desired xylene isomer recovered can exceed the equilibrium value.

Figure 2:
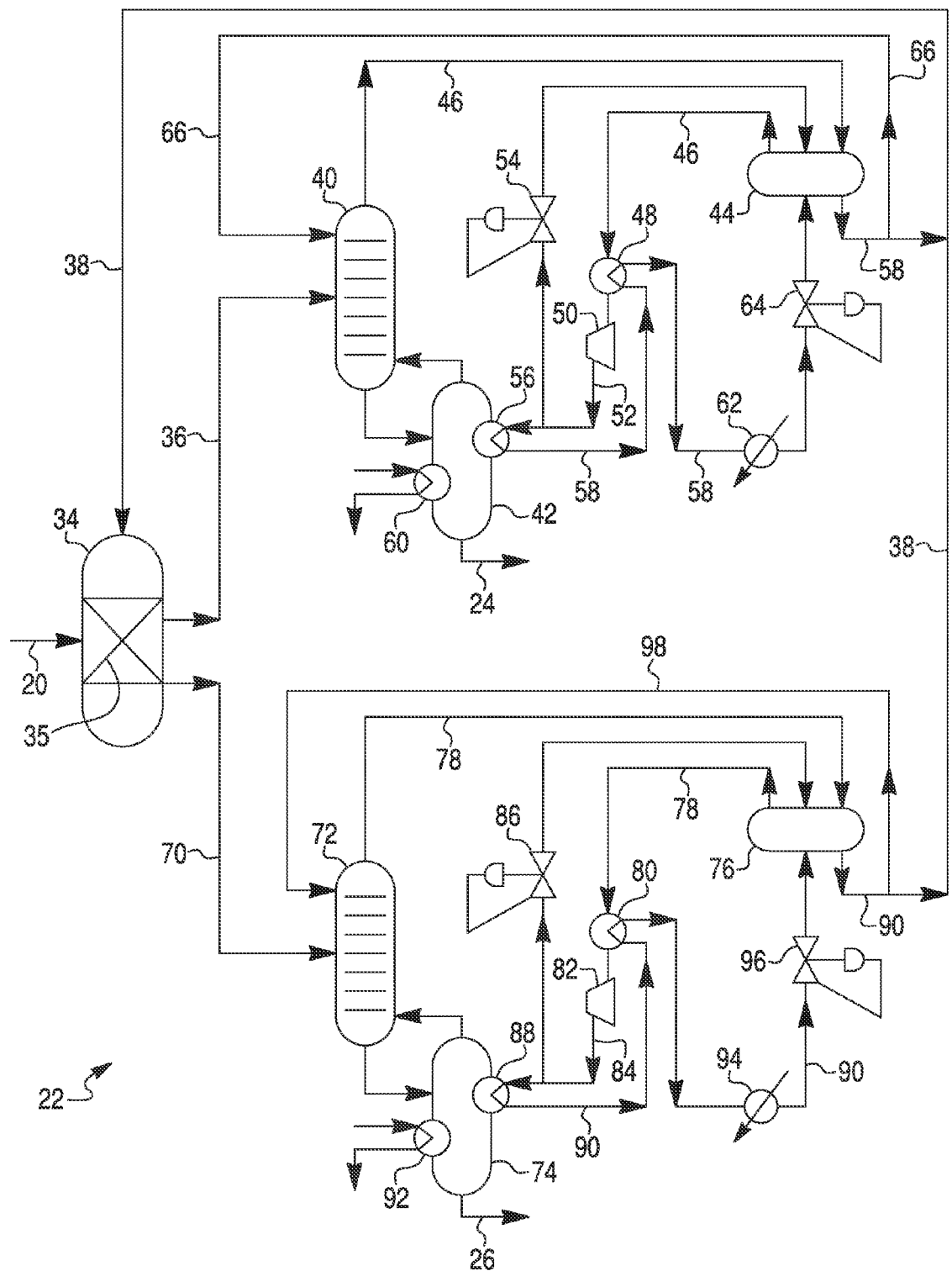
FIG. 2 is a schematic diagram of the isomer recovery unit of the xylene isomer production system if FIG. 1.

Reference is now made to the exemplary embodiment of the isomer recovery unit 22 illustrated in FIG. 2. The mixed xylene stream 20 is introduced to an adsorbent chamber 34 to absorb the desired xylene isomer. The desired xylene isomer is paraxylene in many embodiments, but the desired xylene isomer can also be metaxylene or orthoxylene in other embodiments. The adsorbent chamber 34 includes a selective adsorbent 35 that preferentially adsorbs the desired xylene isomer over the other xylene isomers. In an exemplary embodiment, the selective adsorbent 35 can be crystalline alumino-silicate, such as type X or type Y crystalline aluminosilicate zeolites. The selective adsorbent 35 contains exchangeable cationic sites with one or more metal cations, where the metal cations can be one or more of lithium, potassium, beryllium, magnesium, calcium, strontium, barium, nickel, copper, silver, manganese, and cadmium. Adsorption conditions vary, but typically range from about 35° C. to about 200° C. (about 100° F. to about 400° F.) and from about 100 kPa to about 3,500 kPa (about 14 PSIG to about 500 PSIG).

The mixed xylene stream 20 is separated into an extract stream 36 and a mixed raffinate stream 70 in the adsorbent chamber 34. The selective adsorbent 35 preferentially adsorbs the desired xylene isomer, and the remaining raffinate xylene isomers are discharged with excess desorbent in the mixed raffinate stream 70. Desorbent is charged into the adsorbent chamber 34 by a desorbent stream 38 to desorb the desired xylene isomer, and the mixture of desorbent and desired xylene isomer are discharged in the extract stream 36. Several different embodiments of the adsorbent chamber 34 are possible, such as a single bed operated in batch fashion, where the mixed raffinate stream 70 is collected before the desired xylene isomer is desorbed, and the extract stream 36 is collected after desorbing. In another embodiment, a plurality of adsorbent beds are used, and the introduction point of the mixed xylene stream 20 and the desorbent stream 38 are gradually moved through the different adsorbent beds. The discharge points of the extract stream 36 and the mixed raffinate stream 70 are also gradually moved through the different adsorbent beds, so each individual adsorbent bed is used in a semi-batch mode and the combination simulates a continuous operation. The desorbent has a lower molecular weight than xylene, and a desorbent boiling point lower than that the desired xylene isomer boiling point or a raffinate xylene isomer boiling point. In many embodiments the desorbent is toluene, but other desorbents are possible.

In an exemplary embodiment, the extract stream 36 is introduced into an extract fractionator 40 to separate the desorbent from the desired xylene isomer. The extract fractionator 40 includes an extract process reboiler 56 and an extract overhead receiver 44, where the extract process reboiler 56 and overhead receiver 44 can be either fluidly connected to the main distillation column of the extract fractionator 40, they can be combined in a single unit, or other designs can be used. The extract process reboiler 56 is configured to heat an extract column bottoms 42, which is the liquids at the bottom of the main distillation column of the extract fractionator 40. The desorbent exits the extract fractionator 40 as a vapor in a low pressure extract overhead stream 46, and the desired xylene isomer exits the extract fractionator 40 as a liquid in the desired xylene isomer stream 24. The extract fractionator 40 is operated to maintain the low pressure extract overhead stream 46 between about 100° C. and about 130° C. (about 210° F. to about 270° F.) and a pressure from about 100 kPa to about 150 kPa (about 14 PSIA to about 22 PSIA). This produces an extract reboiler temperature of about 150° C. to about 180° C. (300° F. to 360° F.).

The low pressure extract overhead stream 46 passes through the extract overhead receiver 44 and remains a vapor at essentially the same temperature and pressure when entering the extract overhead receiver 44. In an exemplary embodiment, the low pressure extract overhead stream 46 is heated in a low pressure extract overhead heater 48 to increase the temperature by about 10° C. to about 20° C. prior to pressurization, which increases the low pressure extract overhead stream 46 temperature to about 110° C. to about 150° C. (about 230° F. to about 300° F.). A liquid extract overhead stream 58 (described below) can be used to supply the heat for the low pressure extract overhead heater 48, but in alternate embodiments other heat sources are used.

The low pressure extract overhead stream 46 is pressurized to produce a high pressure extract overhead stream 52, and the temperature increases as the pressure increases. The low pressure extract overhead stream 46 is pressurized to a pressure sufficient to bring the temperature to a point above the extract reboiler temperature of about 150° C. to about 180° C. (about 300° F. to about 360° F.), as described above. In some embodiments, an extract compressor 50 is used to pressurize the low pressure extract overhead stream 46, but other techniques could also be used. In an exemplary embodiment, the pressure is increased by about 200 to about 500 kPa (about 30 to about 70 PSIA), which brings the pressure of the high pressure extract overhead stream to about 300 kPa to about 650 kPa (about 40 to about 90 PSIA), but other pressures are also possible. The temperature of the high pressure extract overhead stream 52 is about 170° C. to about 200° C. (about 340° F. to about 390° F.) after pressurization. The high pressure extract overhead stream 52 remains in the vapor state after pressurization. A high pressure extract overhead pressure regulator 54 can be used to prevent unintentional over pressurization of the high pressure extract overhead stream 52, where the high pressure extract overhead pressure regulator 54 is coupled between the high pressure extract overhead stream 52 and the low pressure extract overhead stream 46, such as at the extract overhead receiver 44.

The vapor in the high pressure extract overhead stream 52 is condensed in the extract process reboiler 56 that is configured to heat the extract column bottoms 42, as mentioned above. The extract process reboiler 56 is a heat exchanger, such as a shell and tube heat exchanger, but other types of heat exchangers can also be used. The gases in the high pressure extract overhead stream 52 provide heat to the extract column bottoms 42 as they condense. The condensed liquid exits the extract process reboiler 56 in a liquid extract overhead stream 58, and the temperature in the liquid extract overhead stream 58 is lower than the temperature in the high pressure extract overhead stream 52. In an exemplary embodiment, the liquid extract overhead stream 58 has a temperature about 2° C. to about 15° C. lower than the temperature of the high pressure extract overhead stream 52. The liquid extract overhead stream 58 can be used to pre-heat the low pressure extract overhead stream 46 in the low pressure extract overhead heater 48, as described above, which can lower the temperature of the liquid extract overhead stream 58 by about 5° C. to about 20° C. The extract fractionator 40 also includes an extract utility reboiler 60 for additional heating, if needed. The extract utility reboiler 60 can be heated by steam, combustion of fuel gas or other fuels, electric heaters, or other techniques known to those skilled in the art. The extract utility reboiler 60 and the extract process reboiler 56 are each configured to heat the extract column bottoms 42, and can be in series, in parallel, or in any configuration suitable for heating the extract column bottoms 42.

The temperature of the liquids in the liquid extract overhead stream 58 may be lowered even further in a liquid extract overhead heat exchanger 62. The temperature is lowered to a point sufficient to prevent the desorbent from boiling in the extract overhead receiver 44, as described more fully below. In one embodiment, the temperature is lowered to below the temperature of the low pressure extract overhead stream 46 in the extract overhead receiver 44, but in other embodiments higher temperatures are used. The liquids in the liquid extract overhead stream 58 remain in the liquid state in the extract overhead receiver 44 when the vapor pressure is less than the actual pressure, and the vapor pressure depends on the temperature. Heat from the liquid extract overhead heat exchanger 62 can be recovered and used elsewhere, such as pre-heating desired process streams, or a coolant can be used to lower the temperature of the liquid extract overhead stream 58.

The pressure in the liquid extract overhead stream 58 is controlled with a liquid extract overhead pressure regulator 64 such that the vapors in the high pressure extract overhead stream 52 are at a temperature above the extract reboiler temperature when condensed in the extract process reboiler 56. The temperature of the liquid extract overhead stream 58 decreases as the pressure is reduced at the extract overhead pressure regulator 64, and the final temperature after the pressure drop is equal to or lower than the temperature in the extract overhead receiver 44. In an exemplary embodiment with toluene as the desorbent and a pressure in the extract overhead receiver 44 at about 100 kPa, the temperature of the liquid extract overhead stream 58 is lowered to a point below about 110° C. by: the (1) low pressure extract overhead heater 48; (2) the liquid extract overhead heat exchanger 62; and (3) the pressure drop at the liquid extract overhead pressure regulator 64. Liquids from the liquid extract overhead stream 58 are then added to the extract overhead receiver 44.

The liquid extract overhead stream 58 flows through the extract overhead receiver 44 and is split into an extract reflux stream 66 and a desorbent stream 38. The extract reflux stream 66 is added to the extract fractionator 40 to aid in controlling distillation, and the desorbent stream 38 is added back to the adsorbent chamber 34 for re-use as the desorbent. In this manner, the desired xylene isomer is recovered free of desorbent in the desired xylene isomer stream 24, and the desorbent is recovered and re-used. Much of the heat needed to evaporate and lift the desorbent into the low pressure extract overhead stream 46 is provided by the extract compressor 50 during the pressurization of the low pressure extract overhead stream 46. In many embodiments, the extract compressor 50 runs on electricity using a motor, so the amount of fuel used in the extract utility reboiler 60 is significantly reduced and replaced by electricity to power the extract compressor 50. The process of pressurizing the overheads and condensing them to heat the reboiler is one type of heat pump operation.

The mixed raffinate stream 70 includes raffinate xylene isomers as well as excess desorbent. The extract stream 36 includes the desired xylene isomer and excess desorbent, and the different xylene isomers have similar physical properties. The raffinate xylene isomers can be separated from the desorbent using equipment and operations very similar to that described above for separating the desired xylene isomer and the desorbent, because the compounds being separated are very similar in nature. Therefore, the equipment, streams, and operating conditions are essentially the same, except for being associated with the mixed raffinate stream 70 instead of the extract stream 36. In various embodiments, the isomer recovery unit 22 can include the fractionation methods and systems described herein for either the extract stream 36 or the mixed raffinate stream 70, or for both, as desired.

In an exemplary embodiment, the equipment for separating the components of the mixed raffinate stream 70 are labeled as indicated below. The terminology is the same as for the extract stream 36, except the word "extract" is replaced with the word "raffinate." The raffinate fractionator 72 has a raffinate process reboiler 88 and a raffinate overhead receiver 76, where the different components of the raffinate fractionator 72 can be combined in different ways in alternate embodiments. The low pressure raffinate overhead stream 78 exits the top of the raffinate fractionator 72, passes through the raffinate overhead receiver 76 and a low pressure raffinate overhead heater 80, and flows to a raffinate compressor 82 to produce a high pressure raffinate overhead stream 84. A high pressure raffinate overhead pressure regulator 86 prevents over pressurization in the high pressure raffinate overhead stream 84, and the high pressure raffinate overhead stream 84 is coupled to the raffinate process reboiler 88. A liquid raffinate overhead stream 90 flows out of the raffinate process reboiler 88. The raffinate fractionator 72 has a raffinate utility reboiler 92 for additional heating, as needed, and the raffinate process reboiler 88 and the raffinate utility reboiler 92 are configured to heat a raffinate column bottoms 74, either individually or together. The liquids in the liquid raffinate overhead stream 90 are cooled in a liquid raffinate overhead heat exchanger 94 and flow to a liquid raffinate overhead pressure regulator 96. The liquid raffinate overhead stream 90 flows through the raffinate overhead receiver 76, and is split into a raffinate reflux stream 98 and the desorbent stream 38, which flows to the raffinate fractionator 72 and the adsorbent chamber 34, respectively.

While at least one exemplary embodiment has been presented in the foregoing detailed description, it should be appreciated that a vast number of variations exist. It should also be appreciated that the exemplary embodiment or exemplary embodiments are only examples, and are not intended to limit the scope, applicability, or configuration of the application in any way. Rather, the foregoing detailed description will provide those skilled in the art with a convenient road map for implementing one or more embodiments, it being understood that various changes may be made in the function and arrangement of elements described in an exemplary embodiment without departing from the scope, as set forth in the appended claims.

The invention claimed is:

1. A method for producing a desired xylene isomer, the method comprising the steps of:
   absorbing the desired xylene isomer from a mixed xylene stream in an adsorbent chamber;
   desorbing the desired xylene isomer with a desorbent to produce an extract stream, wherein the extract stream comprises the desired xylene isomer and the desorbent, and wherein the desorbent has a desorbent boiling point lower than a desired xylene isomer boiling point;
   fractionating the extract stream in an extract fractionator to produce a low pressure extract overhead stream, wherein the low pressure extract overhead stream comprises the desorbent in the gaseous state, and wherein the extract fractionator comprises an extract process reboiler;
   pressurizing the low pressure extract overhead stream to produce a high pressure extract overhead stream, wherein pressurizing the low pressure extract overhead stream produces a high pressure extract overhead stream temperature above an extract reboiler temperature; and condensing the high pressure extract overhead stream in the extract process reboiler to produce a liquid extract overhead stream.

2. The method of claim 1 further comprising: heating the low pressure extract overhead stream with the liquid extract overhead stream.

3. The method of claim 1 further comprising: controlling a pressure of the liquid extract overhead stream with a liquid extract overhead pressure regulator.

4. The method of claim 3 further comprising: cooling the liquid extract overhead stream prior to the liquid extract overhead pressure regulator.

5. The method of claim 1 wherein pressuring the low pressure extract overhead stream further comprises pressurizing the low pressure extract overhead stream with an extract compressor.

6. The method of claim 1 further comprising: adding the liquid extract overhead stream to the adsorbent chamber.

7. The method of claim 1 wherein desorbing the desired xylene isomer with the desorbent further comprises desorbing the desired xylene isomer with the desorbent to produce a mixed raffinate stream comprising a raffinate xylene isomer and the desorbent, and wherein the desorbent boiling point is lower than a raffinate xylene isomer boiling point, the method further comprising:

fractionating the mixed raffinate stream in a raffinate fractionator to produce a low pressure raffinate overhead stream and an raffinate xylene isomer stream, wherein the low pressure raffinate overhead stream comprises the desorbent in the gaseous state, and wherein the raffinate fractionator comprises a raffinate process reboiler;

pressurizing the low pressure raffinate overhead stream to produce a high pressure raffinate overhead stream, wherein pressurizing the low pressure raffinate overhead stream produces a high pressure raffinate overhead stream temperature above a raffinate reboiler temperature; and condensing the high pressure raffinate overhead stream in the raffinate process reboiler to produce a liquid raffinate overhead stream.

8. The method of claim 7 further comprising: fractionating a feed stream in a feed fractionator to produce the mixed xylene stream.

9. The method of claim 8 further comprising:
isomerizing the raffinate xylene isomer stream in an isomerization unit to produce an isomerized stream; and
feeding the isomerized stream to the feed fractionator.

10. A method for producing a desired xylene isomer, the method comprising the steps of:

fractionating a mixed raffinate stream in a raffinate fractionator to produce a low pressure raffinate overhead stream and an raffinate xylene isomer stream, wherein the low pressure raffinate overhead stream comprises a desorbent in the gaseous state, wherein the raffinate fractionator comprises a raffinate process reboiler, and wherein the raffinate xylene isomer stream comprises raffinate xylene isomers different than the desired xylene isomer;

pressurizing the low pressure raffinate overhead stream to produce a high pressure raffinate overhead stream, wherein pressurizing the low pressure raffinate overhead stream produces a temperature of the high pressure raffinate overhead stream above a raffinate reboiler temperature;

condensing the high pressure raffinate overhead stream in the raffinate process reboiler to produce a liquid raffinate overhead stream; and isomerizing the raffinate xylene isomer stream in an isomerization unit to produce the desired xylene isomer.

11. The method of claim 10 further comprising: heating the low pressure raffinate overhead stream with the liquid raffinate overhead stream prior to pressurizing the low pressure raffinate overhead stream.

12. The method of claim 10 further comprising: controlling a liquid raffinate overhead stream pressure with a liquid raffinate overhead stream pressure regulator, wherein the liquid raffinate overhead stream pressure is controlled such that the temperature of the high pressure raffinate overhead stream is above the raffinate reboiler temperature.

13. The method of claim 12 further comprising: cooling the liquid raffinate overhead stream prior to the liquid raffinate overhead stream pressure regulator.

14. The method of claim 10 wherein pressuring the low pressure raffinate overhead stream further comprises pressurizing the low pressure raffinate overhead stream with a raffinate compressor.

15. The method of claim 10 wherein fractionating the mixed raffinate stream in the raffinate fractionator further comprises: Fractionating the mixed raffinate stream in the raffinate fractionator, wherein the raffinate fractionator further comprises a raffinate utility reboiler configured to heat a raffinate column bottoms.

16. The method of claim 10 further comprising:
introducing a mixed xylene stream into an adsorbent chamber to absorb the desired xylene isomer; and
desorbing the desired xylene isomer with the desorbent to produce the mixed raffinate stream comprising the raffinate xylene isomers and the desorbent, and wherein the desorbent has a desorbent boiling point lower than a raffinate xylene isomer boiling point.

17. The method of claim 16 further comprising: adding the liquid raffinate overhead stream to the adsorbent chamber.

18. The method of claim 16 further comprising: fractionating a feed stream in a feed fractionator to produce the mixed xylene stream.

19. The method of claim 18 wherein isomerizing the raffinate xylene isomer stream further comprises producing an isomerized stream, wherein the isomerized stream comprises the desired xylene isomer, the method further comprising: feeding the isomerized stream to the feed fractionator.

* * * * *